(12) United States Patent
Lee et al.

(10) Patent No.: US 7,786,220 B2
(45) Date of Patent: Aug. 31, 2010

(54) PH AND TEMPERATURE SENSITIVE HYDROGELS

(75) Inventors: Doo Sung Lee, Gyeonggi-do (KR); Woo Sun Shim, Gyeonggi-do (KR); You Han Bae, Salt Lake City, UT (US); Je Sun You, Gyeonggi-do (KR); Min Sang Kim, Gyeonggi-do (KR); Huynh Dai Phu, Gyeonggi-do (KR)

(73) Assignee: Sungyunkwan University Foundation for Corporate Collaboration, Suwon-si (KR)

( * ) Notice: Subject to any disclaimer, the term of this patent is extended or adjusted under 35 U.S.C. 154(b) by 660 days.

(21) Appl. No.: 10/590,959

(22) PCT Filed: Jan. 26, 2005

(86) PCT No.: PCT/KR2005/000207

§ 371 (c)(1),
(2), (4) Date: Mar. 12, 2007

(87) PCT Pub. No.: WO2005/073281

PCT Pub. Date: Aug. 11, 2005

(65) Prior Publication Data

US 2007/0244259 A1    Oct. 18, 2007

(30) Foreign Application Priority Data

Jan. 29, 2004    (KR) .................... 10-2004-0005586

(51) Int. Cl.
*C08L 77/00* (2006.01)
(52) U.S. Cl. .................. 525/408; 424/426; 424/486; 514/601; 514/602; 514/603; 514/604; 524/609; 524/612; 524/916
(58) Field of Classification Search .............. 424/486, 424/426; 514/601, 602, 603, 604; 525/408
See application file for complete search history.

(56) References Cited

U.S. PATENT DOCUMENTS

| 4,176,203 | A |  | 11/1979 | Lagerstrom |
|---|---|---|---|---|
| 4,882,168 | A |  | 11/1989 | Casey et al. |
| 4,942,035 | A |  | 7/1990 | Churchill et al. |
| 5,476,909 | A |  | 12/1995 | Kim et al. |
| 5,548,035 | A |  | 8/1996 | Kim et al. |
| 6,103,865 | A | * | 8/2000 | Bae et al. .................... 528/373 |
| 6,541,033 | B1 | * | 4/2003 | Shah .......................... 424/486 |

FOREIGN PATENT DOCUMENTS

| JP | 9-136921 A | 5/1997 |
|---|---|---|
| JP | 2000-80158 A | 3/2000 |
| KR | 97-701739 A | 4/1997 |
| KR | 2000-12970 A | 3/2000 |
| KR | 1020000012970 | 3/2000 |
| KR | 1020010081362 | 8/2001 |

OTHER PUBLICATIONS

Seung Kil Han, Kun Na, You Han Bae; Colloids and Surfaces A: Physiochem. Eng. Aspects, 214 (2003) 49-59.*
Ming-Hsi Huang, Suming Li, Jean Coudane, Michel Vert; Macromol. Chem. Phys. 2003, 204, 1994-2001.*
Deng, X. et al., "Synthesis and Characterization of Biodegradable Block Copolymers of e-Caprolactone and D,L-Lactide Initiated by Potassium Poly(ethylene glycol)ate," J. of Polyer Science, Part A: Polymer Chemistry, vol. 35, 703-708 (1997).

* cited by examiner

*Primary Examiner*—David Wu
*Assistant Examiner*—Robert Jones, Jr.
(74) *Attorney, Agent, or Firm*—Sughrue Mion, PLLC

(57) ABSTRACT

The present invention relates to a block copolymer formed by coupling the following components with each other, as well as a hydrogel composition comprising the block copolymer and a hydrogel formed from the composition: (a) a copolymer of a polyethylene glycol (PEG)-based compound with a biodegradable polymer; and (b) a sulfonamide-based oligomer. The inventive block copolymer shows the sol-gel transition behavior sensitive to changes in not only temperature but also pH. Thus, the inventive block copolymer overcomes the shortcomings of temperature-sensitive copolymers, form a more strong and stable hydrogel, and is stable in vivo. Accordingly, the inventive block copolymer can be used in various applications in the medical and drug delivery fields.

15 Claims, 7 Drawing Sheets

FIG. 1
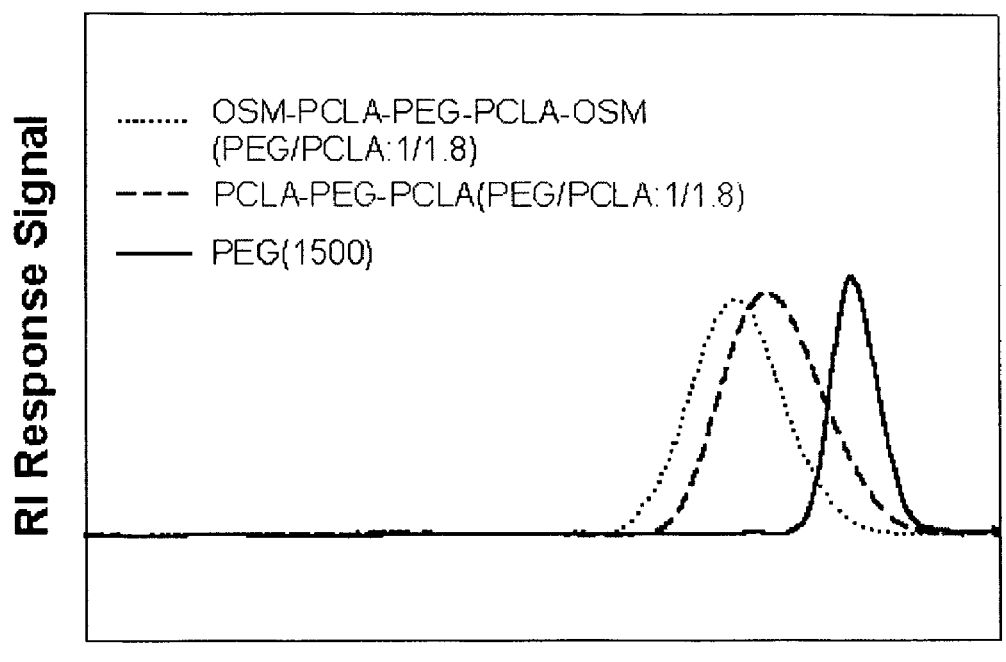
FIG. 2
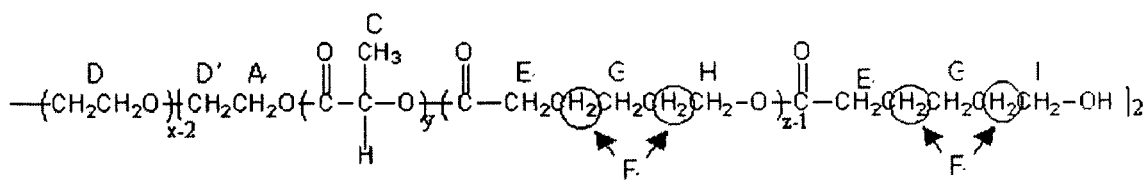
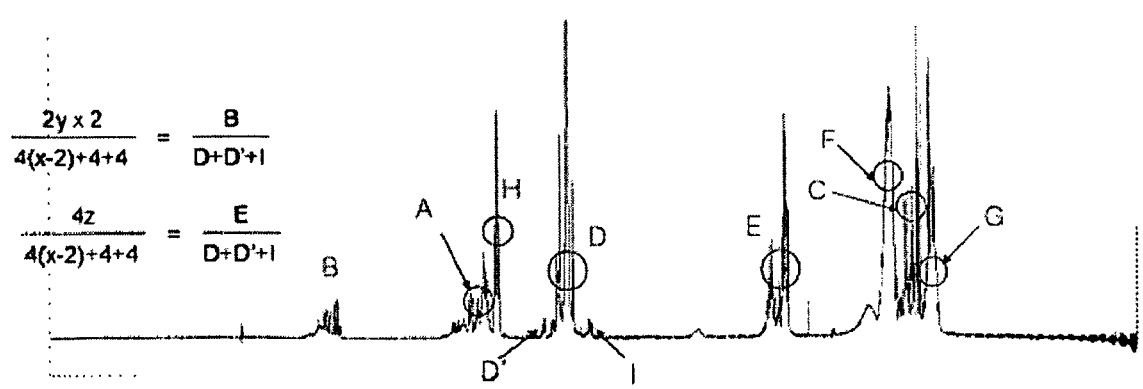

FIG. 4
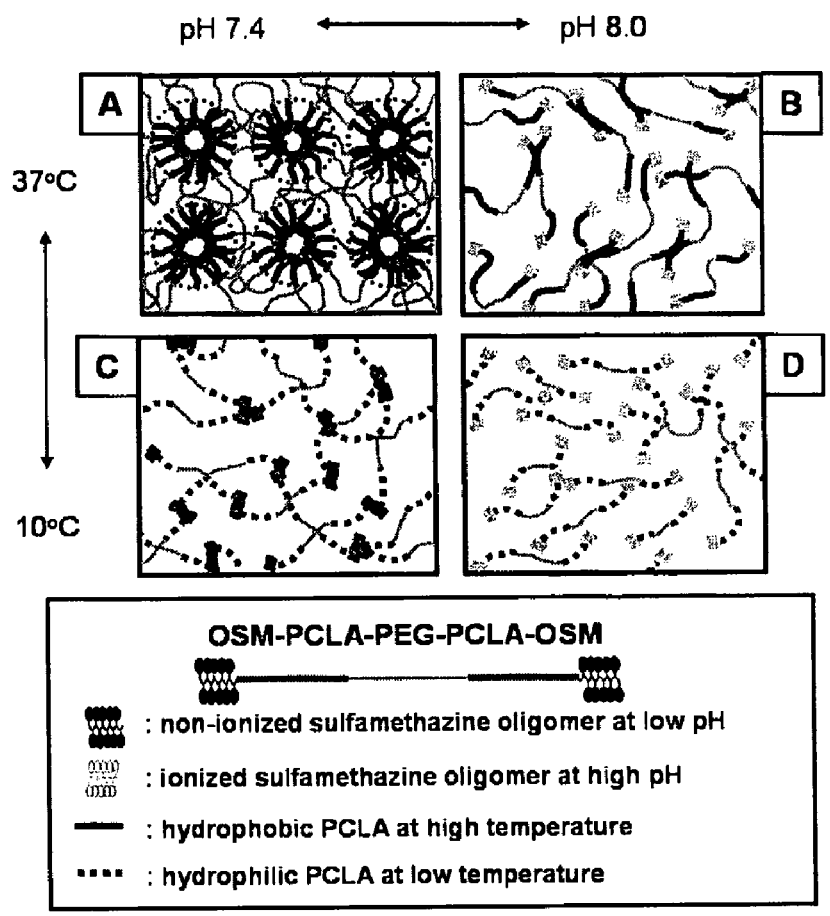
FIG. 5
Injection　　　　　　　　　Shaking
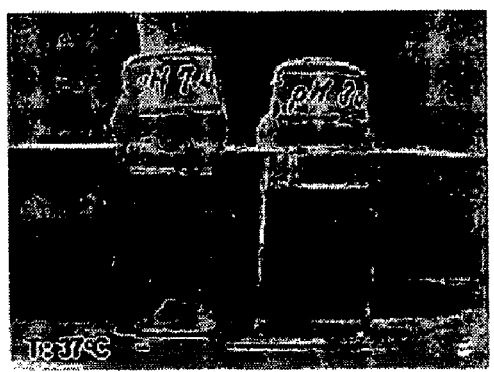
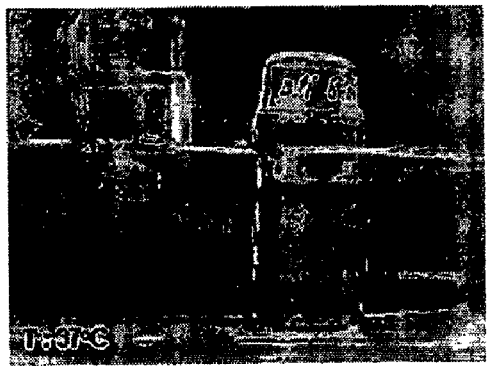

Adding buffer solution(pH=7.4) → 37°C After 2 weeks

PH AND TEMPERATURE SENSITIVE HYDROGELS

TECHNICAL FIELD

The present invention relates to a pH- and temperature-sensitive block copolymer, a hydrogel composition containing the block copolymer, and a hydrogel prepared from the composition. More particularly, the present invention relates to a block copolymer formed by coupling the following components with each other, as well as a hydrogel composition containing the block copolymer and a hydrogel prepared from the composition: (a) a copolymer of a polyethylene glycol-based compound with a biodegradable polymer; and (b) a sulfonamide-based oligomer.

BACKGROUND ART

Amphiphilic polymers having both hydrophobicity and hydrophilicity have been of interest. Particularly, amphiphilic polymers that exhibit a temperature-sensitive sol-gel behavior are now studied intensively in the drug delivery system and medical fields, and studies on their use are also actively conducted. Particularly, copolymers composed of polyethylene oxide and polypropylene oxide are commercially available under the trade names Pluronic and Poloxamer and used in various applications.

However, the Pluronic- and Poloxamer-based polymers encountered problems upon use in medical applications due to non-biodegradability. For this reason, copolymers composed of biodegradable polylactide (PLA) (or polyglycolide (PGA), polycaprolactone (PCL) and a copolymer thereof) and polyethylene glycol (PEG) have been studied and used.

U.S. Pat. Nos. 4,882,168 and 4,716,203 disclose copolymers of hydrophilic polyalkylene glycol with polyglycolic acid, trimethylene carbonate and the like.

Furthermore, U.S. Pat. No. 4,942,035 discloses a pharmaceutical composition comprising a block copolymer of polyethylene glycol (PEG) with polylactide (PLA), polyglycolide (PGA), polycaprolactone (PCL), hydrophobic polypeptide or polyacetal.

Moreover, U.S. Pat. No. 5,476,909 discloses a biodegradable triblock (A-B-A) copolymer consisting of: hydrophobic blocks (A) comprising polylactide (PLA), polyglycolide (PGA) or derivatives thereof, and a hydrophilic block (B) comprising polyethylene glycol (PEG) or its derivatives.

And, U.S. Pat. No. 5,548,035 discloses a biodegradable multi-block copolymer with thermoplasticity comprising a hydrophobic block selected from polylactide, polyglycolic acid, a copolymer thereof, and polycaprolactone.

Meanwhile, Korean Patent Laid-Open Publication No. 2000-0012970 (Mar. 6, 2000) discloses a pH-sensitive polymer comprising sulfonamide groups, and a preparation method thereof. This patent relates mainly to either a change in the solubility of linear polymers formed by the random copolymerization of sulfonamide monomers with DMAAm or NiPAAm, or the swelling index of crosslinked polymers thereof.

The above-described prior arts were so designed that a sol-gel transition phenomenon is shown by the use of the block copolymer of the hydrophobic biodegradable polymer with the hydrophilic polymer. The block copolymer when injected in vivo in an aqueous solution form, a sol state, is changed into a gel state. Thus, the block copolymer was used as a sustained-release drug delivery system which carries and slowly releases drugs in vivo.

However, block copolymers that exhibit a temperature sensitive sol-gel transition phenomenon cause problems, such as the clogging phenomenon of injection needles occurring during injection before in vivo injection, since in vivo temperature and the temperature of the injection needles are adjusted to the same temperature by thermal equilibrium. In addition, hydrophobic moieties comprised of PLA, PLGA or PCL are reported to exhibit pH sensitivity. However, such moieties are not so sensitive that they can be applied to in vivo pH, and thus, they are not suitable for practical use in the drug delivery field.

BRIEF DESCRIPTION OF THE DRAWINGS

FIG. 1 is a graphic diagram showing the results of gel permeation chromatography (GPC) for a block copolymer (OSM-PCLA-PEG-PCLA-OSM) prepared in Example 1.

FIG. 2 is a graphic diagram showing the results of $^1$H-NMR analysis for a block copolymer (PCLA-PEG-PCLA) prepared in Example 1.

FIG. 4 is a schematic diagram showing the sol-gel transition mechanisms of block copolymers (OSM-PCLA-PEG-PCLA-OSM) prepared in Examples 1 and 2.

FIG. 5 depicts photographs showing that a block copolymer (OSM-PCLA-PEG-PCLA-OSM) prepared in Example 1, after injected into each of buffer solution 1 (pH=7.4, 37° C.) and buffer solution 2 (37° C., pH=8.0) in a sol state, forms gel in the buffer solution 1 and is dissolved in the buffer solution 2.

DISCLOSURE OF THE INVENTION

Figure 3:
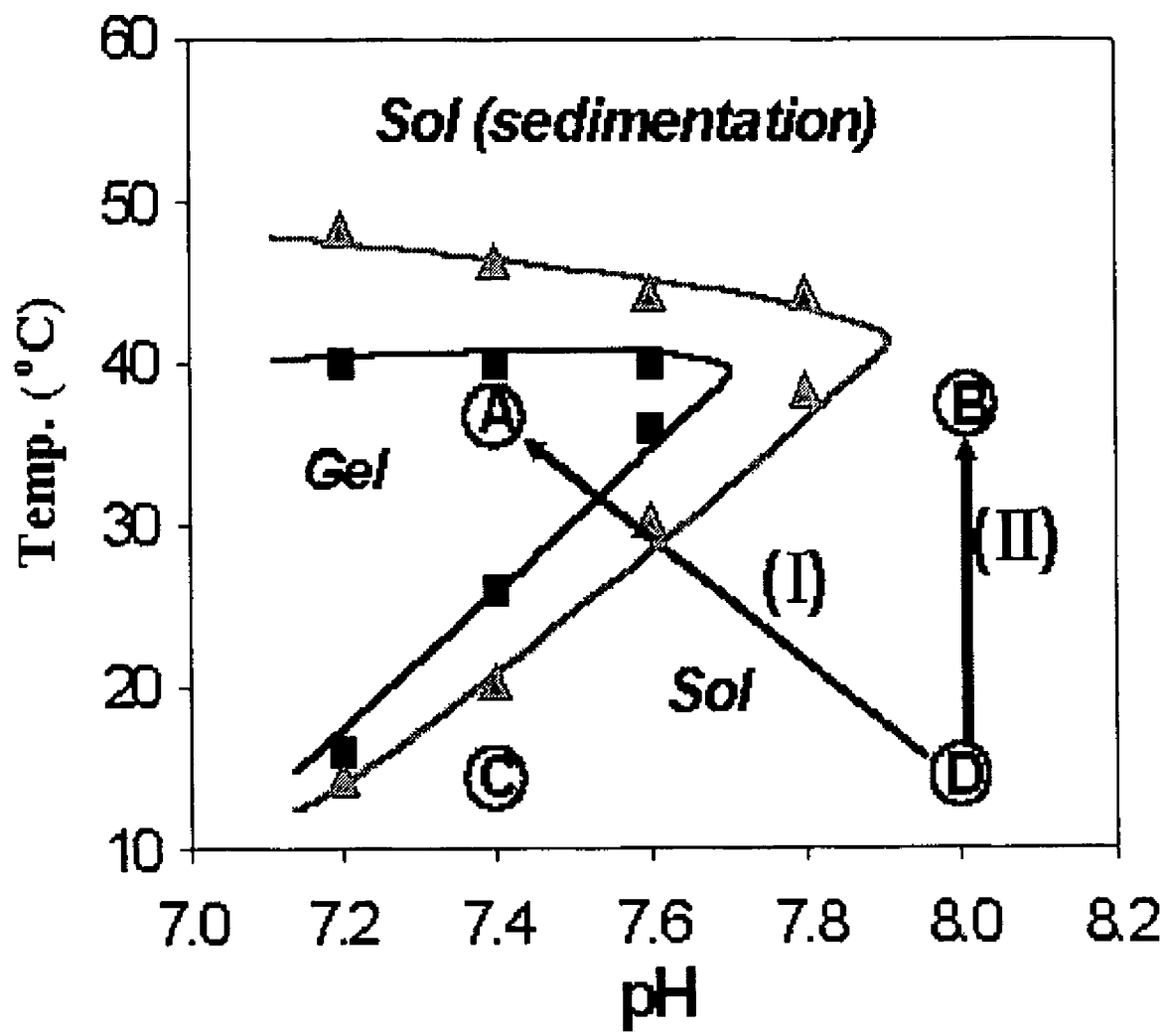
FIG. 3 is a graphic diagram showing the sol-gel transition behaviors of block copolymers (OSM-PCLA-PEG-PCLA-OSM) prepared in Examples 1 and 2, caused by changes in temperature and pH.

The present invention has been made to solve the above-described problems occurring in the prior art, and it is an object of the present invention to provide a novel pH- and temperature-sensitive block copolymer which shows a sol-gel transition behavior sensitive to not only temperature but also pH, and thus becomes gel around pH 7-7.4 similar to in vivo pH and sol at a higher pH than this pH range, so that, when the block copolymer is dissolved at high pH and injected in vivo, it can show a gel state in vivo.

To achieve the above object, the present invention provides a block copolymer formed by coupling the following components with each other, as well as hydrogels containing the block copolymer, and a hydrogel formed from the components: (a) a copolymer of a polyethylene glycol-based compound with a biodegradable polymer; and (b) a sulfonamide-based oligomer.

Hereinafter, the present invention will be described in detail.

The present invention is characterized in that a sulfonamide-based oligomer showing a change in ionization degree with a change in pH (pH sensitivity) is coupled to a copolymer of a hydrophilic PEG-based compound with a biodegradable polymer, thus forming a novel block copolymer which can be used in actual drug delivery.

Because of the characteristic as described above, the inventive block copolymer shows a sol-gel transition behavior sensitive to not only temperature but also pH.

Namely, the prior block copolymer composed of a hydrophobic biodegradable polymer and a hydrophilic polymer showed a sol-gel transition behavior caused by a change in the physical properties of each of the hydrophobic block and the hydrophilic block with a change in temperature. However, due to the in vivo incompatibility of the block copolymer caused by the thermal equilibrium of a delivery medium, it was difficult to apply the block copolymer in actual drug delivery.

However, according to the present invention, the sulfonamide-based oligomer that shows a change in ionization degree with a change in pH is coupled to the copolymer composed of the hydrophobic biodegradable polymer and the hydrophilic polymer so as to impart pH sensitivity in addition to temperature sensitivity to the copolymer. This can solve the above-described problem with the temperature-sensitive hydrogels. Also, the temperature- and pH-sensitive block copolymer according to the present invention forms a more stable hydrogel and is stable in vivo, and thus, it can be applied in the medical and drug delivery fields, particularly as sustained-release drug delivery systems which carry and release drugs.

One component of the temperature- and pH-sensitive block copolymer according to the present invention is the copolymer (a) of the PEG-based compound with the biodegradable polymer. The copolymer (a) has not only the hydrophilicity of the PEG-based compound but also the hydrophobicity of the biodegradable polymer, so that it can show sol-gel transition by a change in temperature.

As the PEG-based compound contained in the copolymer (a), any conventional PEG-based compound known in the art may be used. Particularly, a PEG-based compound represented by the following formula 1, such as PEG or methoxy PEG, is preferred:

[Formula 1]

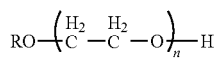

wherein R represents a hydrogen atom or an alkyl group containing 1 to 5 carbon atoms, and n is a natural number ranging from 11 to 45.

The molecular weight of the polyethylene glycol-based compound is preferably 500-2,000. Particularly, the molecular weight of polyethylene glycol (PEG) where R in the formula 1 represents hydrogen is preferably 1,000-2,000, and the molecular weight of methoxy polyethylene glycol where R represents a methyl group is preferably 500-2,000. If the molecular weight is less than 500 or more than 2,000, there will be problems in that gel formation does not occur well, or otherwise, even if gel is formed, gel formation under in vivo conditions (37° C.) does not occur.

As the biodegradable polymer contained in the copolymer (a), any conventional biodegradable polymer known in the art may be used and examples thereof include, but are not limited to, caprolactone (CL), glycolide (GA), lactide (LA) and copolymers thereof.

Examples of the copolymer (a) formed by the polymerization of the polyethylene glycol-based compound with the biodegradable polymer include, but are not limited to, polylactide (PLA), polyglycolide (PGA), polycaprolactone (PCL), poly(caprolactone-lactide) random copolymer (PCLA), poly(caprolactone-glycolide) random copolymer (PCGA) or poly(lactide-glycolide) random copolymer (PLGA).

The molecular weight ratio of the PEG-based compound to the biodegradable polymer in the copolymer (a) is not limited to any special range, but is preferably in a range of 1:1-3. If the molecular weight ratio is less than 1:1, the block copolymer will not form gel, and if it is more than 1:3, the magnitude of hydrophobicity of the block copolymer will be increased such that the block copolymer cannot be dissolved.

Moreover, in the case where the biodegradable polymer in the copolymer is PCLA, PCGA or PLGA, its molar ratio can be suitably controlled so as to increase the temperature- and pH-sensitivity effect of the block copolymer.

As another component of the temperature- and pH-sensitive block copolymer according to the present invention, a compound that shows a change in ionization degree with a change in pH may be used. Particularly, the oligomer (b) formed from a sulfonamide-based compound is preferably used. The sulfonamide-based oligomer preferably contains functional groups, such as hydroxyl groups (—OH), carboxyl groups (—COOH) or amine groups (—NH$_2$). This makes it easy to prepare the inventive block copolymer by polymerization reaction.

Examples of the sulfonamide-based compound for use in forming the oligomer (b) include, but are not limited to, sulfamethisole, sulfamethazine, sulfasetamide, sulfisomidine, sulfafenasole, sulfamethoxasole, sulfadiazine, sulfamethoxydiazine, sulfamethoxypyridazine, sulfadoxine, sulfapyridine, sulfabenzamide, sulfisoxazole or derivatives thereof.

The molecular weight of the oligomer formed from the sulfonamide-based compound is not specifically limited, but is preferably 500-2,000. If the molecular weight is less than 500, the block copolymer will not show a sol-gel transition behavior caused by a change in pH, and if it is more than 2,000, the block copolymer will be difficult to exhibit temperature sensitivity as well.

The inventive copolymer formed by coupling the above-described components (i.e., the copolymer of the PEG-based compound with the biodegradable polymer (a) and the sulfonamide-based oligomer (b)) to each other is preferably in the form of a triblock or higher order multiblock copolymer, particularly a triblock or pentablock copolymer. Specific examples of the triblock or pentablock copolymer include a compound represented by the following formula 2 (OSM-PCLA-PEG-PCLA-OSM), a compound represented by the following formula 3 (MPEG-PCLA-OSM), and a compound represented by the following formula 4 (OSM-PCGA-PEG-PCGA-OSM):

[Formula 2]
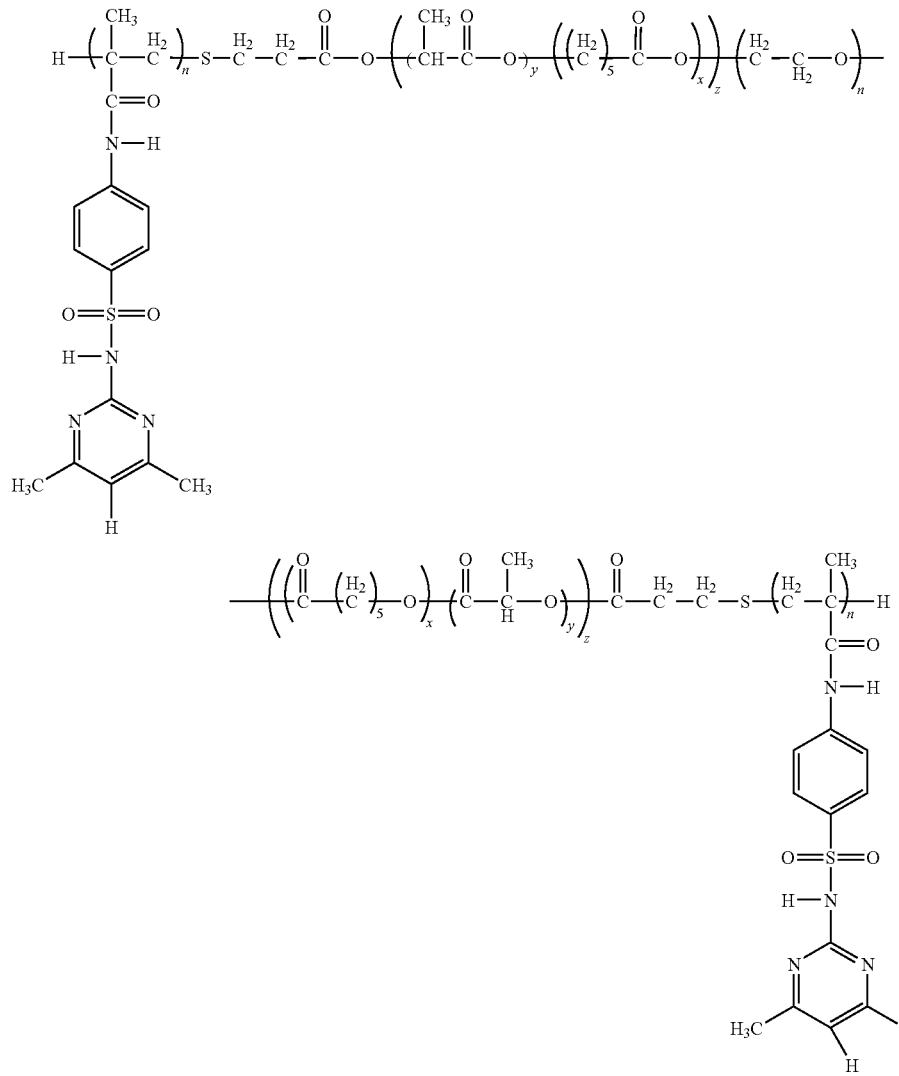
[Formula 3]
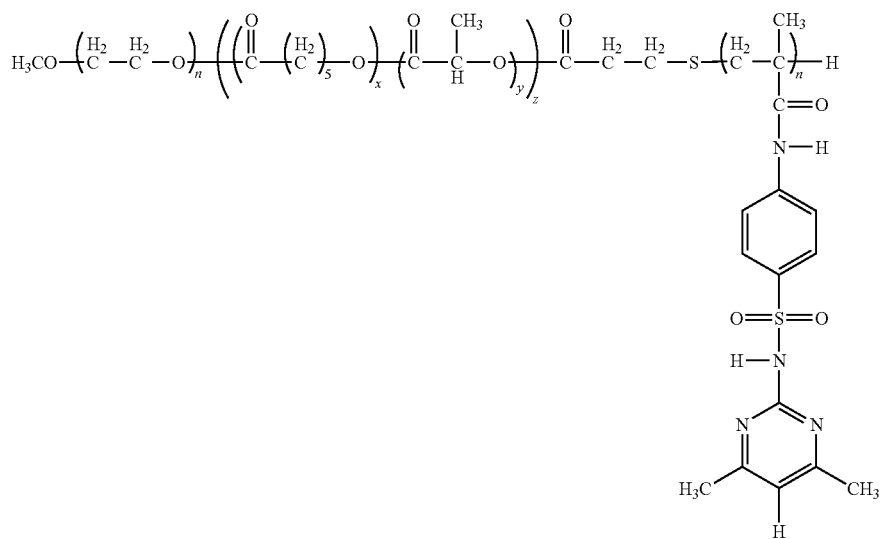

-continued

[Formula 4]

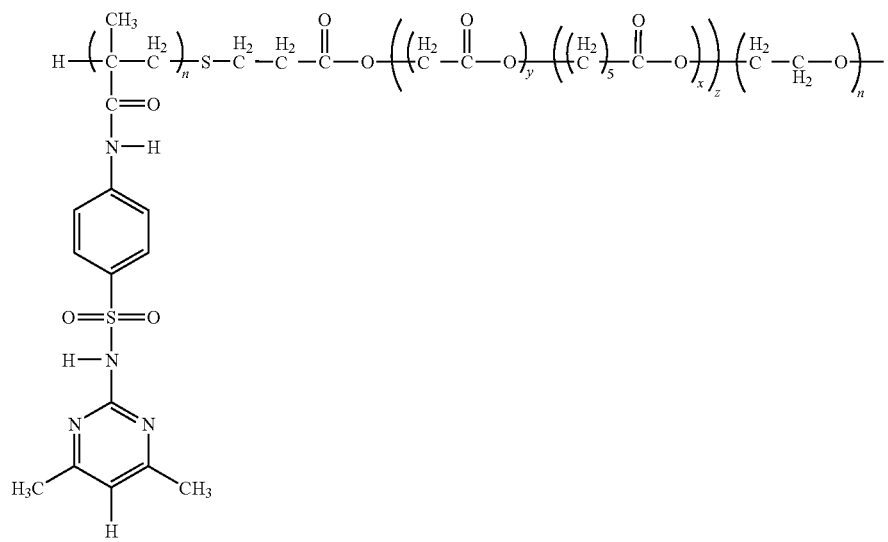

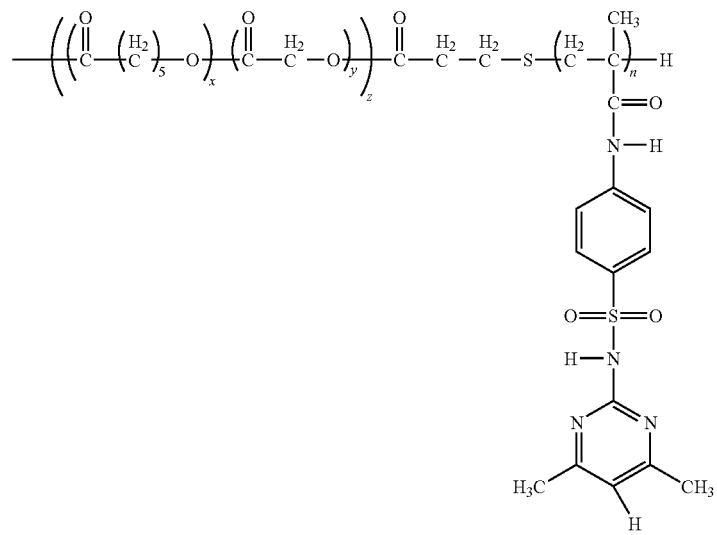

The block copolymer represented by the formula 3 has a block structure with a sulfamethazine oligomer coupled to only one side thereof, because there is a hydroxyl group at only one end of the copolymer of the PEG-based compound with the biodegradable polymer (MPEG-PCLA).

The temperature- and pH-sensitive block copolymer according to the present invention may contain, in addition to the above-described components, other components or additives which are conventionally used in the art.

To prepare the temperature- and pH-sensitive block copolymer from the copolymer (a) of the PEG-based compound with the biodegradable polymer; and the sulfonamide-based oligomer (b), any polymerization method known in the art, such as radical polymerization, cationic polymerization, anionic polymerization, condensation polymerization or the like, may be used.

One embodiment of a method for preparing the temperature- and pH-sensitive block copolymer according to the present invention comprises the steps of: a) polymerizing a PEG-based compound with a biodegradable polymer so as to prepare a copolymer; b) preparing a sulfonamide-based oligomer from a sulfonamide-based compound; and c) coupling the copolymer of the step a) with the oligomer of the step b).

First, 1) the PEG-based compound is polymerized with the biodegradable polymer so as to form a copolymer. This polymerization reaction can be illustrated by, for example, the following reaction scheme 1:

[Reaction Scheme 1]
(1)
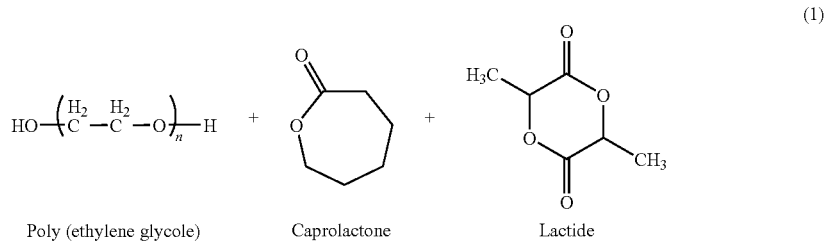
Poly (ethylene glycole)  Caprolactone  Lactide
(2)
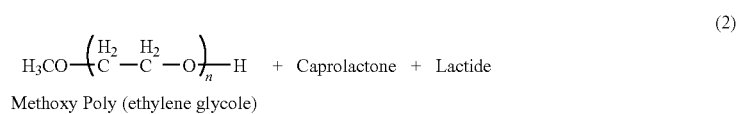
Methoxy Poly (ethylene glycole) + Caprolactone + Lactide
(3)
Poly (ethylene glycole) + Caprolactone + Glycolide
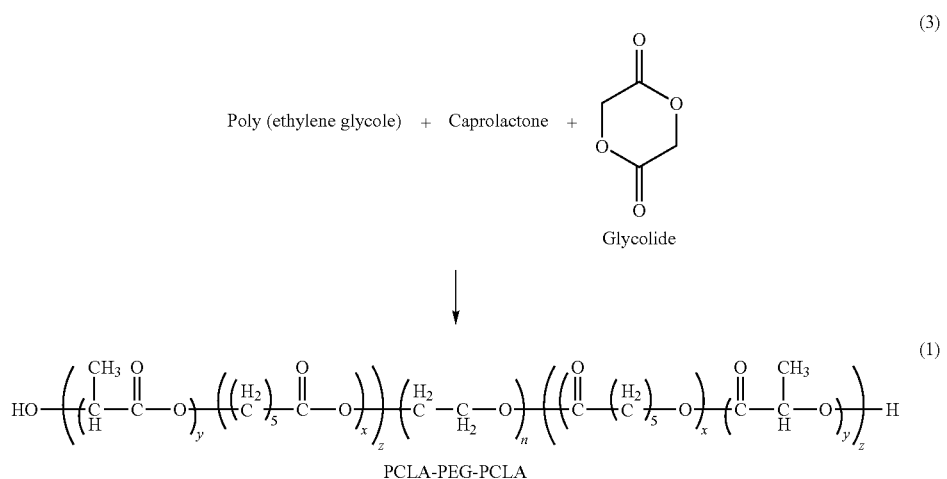
(1)
PCLA-PEG-PCLA
(2)
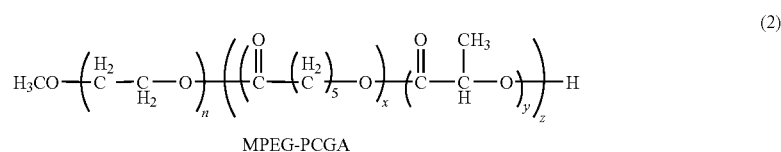
MPEG-PCGA
(3)
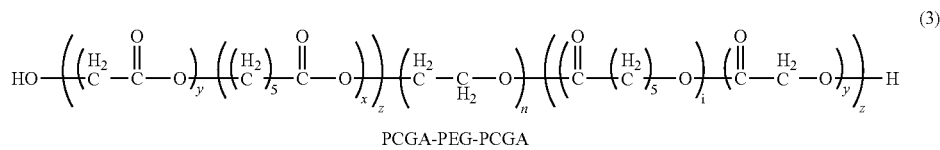
PCGA-PEG-PCGA Ring opening polymerization is preferably used, in which case the polymerization temperature and time are not specifically limited, but are 130-150° C. and 12-48 hours, respectively. Moreover, a catalyst may also be used in the polymerization reaction, and examples thereof include stannous octoate, stannous chloride, metal oxide (GeO$_2$, Sb$_3$O$_2$, SnO$_2$, etc), aluminum triisopropoxide, CaH$_2$, Zn, lithium chloride, tris(2,6-di-tert-butylphenolate), and the like. Also, in order to make the magnitude of hydrophobicity wide, the molecular weight or kind of the above-described biodegradable polymer can be suitably controlled.

2) The oligomer is prepared from the sulfonamide-based compound. This reaction can be illustrated by, for example, the following reaction scheme 2:

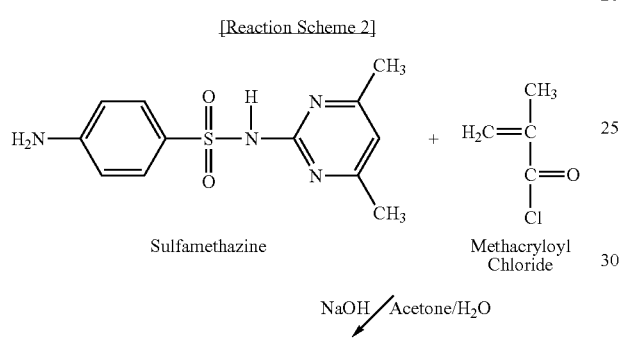

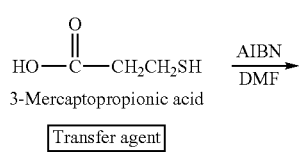

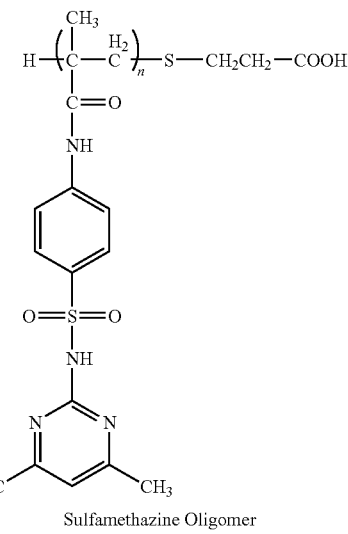

Sulfamethazine Oligomer

Examples of a chain transfer agent (CTA) which can be used in the preparation of the sulfonamide-based oligomer include C8-C18 alkyl mercaptans, organic halogen compounds, α-methylstyrene dimers, terpinolene, α-terpinene, and the like. The chain transfer agents may be selected depending on purpose. Particularly, mercaptans are preferred because they have high chain transfer constant and chain transfer efficiency.

Any initiator known in the art may be used and examples thereof include, but are not limited to, 2,2'-azobisisobutyronitrile (AIBN), 2,2'-azobis-(2,4-dimethylvaleronitrile), 2,2'-azobis-(4-methoxy-2,4-dimethylvaleronitrile), benzoylperoxide, lauroylperoxide, t-butylperoxypivalate, 1,1'-bis-(bis-t-butylperoxy)cyclohexane, and the like.

For coupling to the copolymer of the PEG-based compound with the biodegradable polymer, the sulfonamide-based oligomer preferably contains, in a molecule, hydrophilic functional groups, for example, hydroxyl, carboxyl or amine groups.

3) The temperature- and pH-sensitive block copolymer according to the present invention can be prepared by the coupling between the copolymer (a) of the PEG-based compound with the biodegradable polymer; and the sulfonamide-based oligomer (b). This coupling reaction can be illustrated by the following reaction scheme 3:

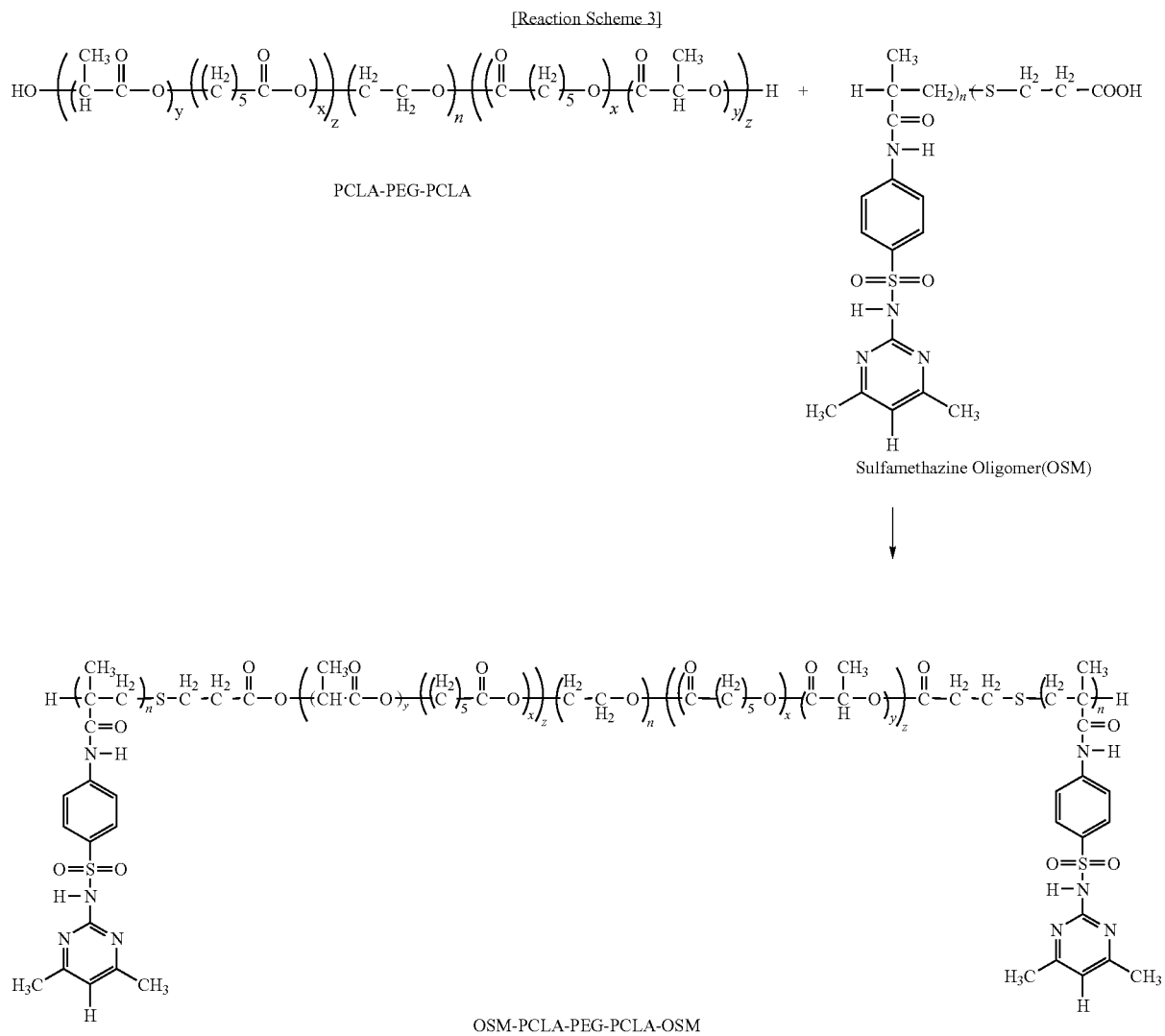

[Reaction Scheme 3]

PCLA-PEG-PCLA

Sulfamethazine Oligomer(OSM)

OSM-PCLA-PEG-PCLA-OSM

The reaction temperature and time in the step 3) are not specifically limited, and the coupling reaction may be performed by any method known in the art.

The block copolymer prepared by the above-described method can show sensitivity to not only temperature but also pH, because it is in a form where the hydrophilic block, the hydrophobic block, and the sulfonamide-based oligomer which shows a change in ionization degree with a change in pH, are coupled with each other as described above. Actually, in a sulfamethazine-polycaprolactone/lactide-polyethylene glycol-polycaprolactone/lactide-sulfamethazine (OSM-PCLA-PEG-PCLA-OSM) block copolymer prepared by the above-described method, the introduction of functional groups and the reaction of terminal groups could be confirmed by FT-IR and $^1$H-NMR. Also, it could be confirmed by gel permeation chromatography (GPC) that the molecular weight of the block copolymer was increased, indicating that the copolymer of the PEG-based compound with the biodegradable polymer and the sulfonamide-based compound were coupled with each other.

Also, in order to determine if the block copolymer has pH sensitivity, a change in sol-gel transition behavior was measured while changing pH with temperature, and the measurement results demonstrated that the inventive block copolymer has pH-sensitive characteristics.

In another aspect, the present invention provides a hydrogel composition comprising the inventive block copolymer. This composition may additionally contain other additives and solvent known in the art.

In addition, the present invention provides a new hydrogel formed from the hydrogel composition by changes in temperature and pH. The hydrogel may be applied in various applications in the medical and drug delivery fields.

BEST MODE FOR CARRYING OUT THE INVENTION

Hereinafter, the following examples will be presented for a better understanding of the present invention. It is to be understood, however, that these examples are given for illustrative purpose only and are not construed to limit the scope of the present invention.

EXAMPLES 1-9

Preparation of Temperature- and pH-Sensitive Block Copolymers

Example 1

OSM-PCLA-PEG-PCLA-OSM Pentablock Copolymer (1)

1-1: PCLA-PEG-PCLA Copolymer (1)

10 g of PEG (Mn=1500) and 0.2 g of catalyst stannous octoate were placed into a reactor and dried under vacuum at 110° C. for 4 hours to remove moisture. The dried substance was cooled under a nitrogen atmosphere, to which 13.68 g of ε-caprolactone and 4.32 g of D,L-lactide were added. The reaction mixture was heated slowly to 135° C. under a nitrogen atmosphere, followed by polymerization for 24 hours. After completion of the reaction, the reaction mixture was cooled to ambient temperature and dissolved by the addition of a small amount of methylene chloride. The dissolved reaction mixture was precipitated in an excess of ethyl ether to remove unreacted substances, and the product was vacuum-dried at 40° C. for 48 hours. The yield of the product was 85%.

The molecular weight of the synthesized PCLA-PEG-PCLA was calculated from the already known molecular weight of PEG and the integration value of the characteristic peak of H in each block among $^1$H-NMR analysis results (see FIG. 2). The $^1$H-NMR analysis results were as follows: the molecular weight ratio of PEG/PCLA in the block copolymer=1/1.85; and the molar fraction of caprolactone (CL) to lactide (LA) in the PCLA block=2.44/1.

1-2: Sulfamethazine Oligomer (OSM)

27.83 g (0.1 mol) of sulfamethazine was dissolved in 100 ml of an acetone/water co-solvent system containing 4 g (0.1 mol) of sodium hydroxide dissolved therein. To this solution, 12.54 g (0.12 mol) of methacroyl chloride was slowly added dropwise, thus obtaining 34.5 g (85% yield) of a sulfamethazine monomer having double bond. The reaction to form the monomer was carried out in an ice bath for 3 hours. The synthesized sulfamethazine monomer which has been precipitated in the reaction solvent was then filtered and vacuum-dried at ambient temperature for 48 hours. The prepared sulfamethazine monomer was allowed to react with 3-mercaptopropionic acid using initiator AIBN in a DMF solvent under a nitrogen atmosphere at 85° C. for 48 hours. Here, the molar equivalent ratio of sulfamethazine monomer:3-mercaptopropionic acid:initiator was 1:0.1:0.1. After completion of the reaction, the DMF solvent was removed by an evaporator, after which the reaction mixture was dissolved again in THF. The dissolved reaction mixture was precipitated in an excess of ethyl ether, thus obtaining more than 90% yield of a sulfamethazine oligomer with a terminal carboxyl group. The results of GPC analysis showed that the oligomer had a molecular weight (Mn) of 1144.

1-3: OSM-PCLA-PEG-PCLA-OSM Block Copolymer (1)

The PCLA-PEG-PCLA block copolymer prepared in Example 1-1 was placed into a reactor and vacuum-dried at 85° C. to remove moisture. Next, the reaction substance was cooled to ambient temperature, to which the sulfamethazine oligomer prepared in Example 1-2 was then added under a nitrogen atmosphere. Then, anhydrous methylene chloride containing coupling agent DCC and catalyst DMAP dissolved therein was added. Here, the molar equivalent ratio of PCLA-PEG-PCLA:sulfamethazine oligomer:DCC:DMAP was 1:2.4:2.8:0.28. The reaction mixture was allowed to react at ambient temperature for 48 hours under a nitrogen atmosphere. The reaction was a heterogeneous reaction in which the sulfamethazine oligomer was not dissolved in methylene chloride. After completion of the reaction, unreacted sulfamethazine oligomer could be removed by filtering. The filtered reaction mixture was precipitated in an excess of ethyl ether, and then vacuum-dried at 40° C. for 48 hours, thus obtaining more than 60% yield of the final product. An increase in the molecular weight of the product was confirmed by GPC analysis (see FIG. 1).

Example 2

OSM-PCLA-PEG-PCLA-OSM Pentablock Copolymer (2)

The block copolymer was prepared in the same manner as in Example 1 except that the molecular weight ratio of PEG/PCLA and the molar fraction of CL/LA were changed from 1/1.85 and 2.44/1 to 1/2.08 and 2.59/1, respectively.

Example 3

OSM-PCLA-PEG-PCLA-OSM Pentablock Copolymer (3)

The block copolymer was prepared in the same manner as in Example 1 except that PEG (Mn=1750) was used in place of PEG (Mn=1500).

Example 4

OSM-PCLA-PEG-PCLA-OSM Pentablock Copolymer (4)

The block copolymer was prepared in the same manner as in Example 1 except that PEG (Mn=2000) was used in place of PEG (Mn=1500).

Example 5

OSM-PCLA-PEG-PCLA-OSM Pentablock Copolymer (5)

The block copolymer was prepared in the same manner as in Example 1 except that a sulfamethazine oligomer (Mn=937) was used in place of the sulfamethazine (Mn=1144).

Example 6

MPEG-PCLA-OSM Block Copolymer (1)

The MPEG-PCLA-OSM triblock copolymer was prepared in the same manner as in Example 1 except that MPEG-PCLA prepared with the use of methoxy poly(ethylene glycol) was used in place of PEG (Mn=1500), and the molar equivalent ratio of MPEG-PCLA:sulfamethazine oligomer:DCC:DMAP=1:1.2:1.4:0.14. In the block copolymer prepared in this Example, the molecular weight ratio of MPEG/PCLA was 1/1.86, and the molar fraction of caprolactone (CL) to lactide (LA) in the PCLA block was 2.67/1.

Example 7

MPEG-PCLA-OSM Block Copolymer (2)

The MPEG-PCLA-OSM triblock copolymer was prepared in the same manner as in Example 6 except that the molecular weight ratio of MPEG/PCLA and the molar fraction of caprolactone (CL)/lactide (LA) in the PCLA block were changed from 1/1.86 and 2.67/1 to 1/2.04 and 2.70/1, respectively.

Example 8

OSM-PCGA-PEG-PCGA-OSM Block Copolymer (1)

The pentablock copolymer was prepared in the same manner as in Example 1 except that PCGA-PEG-PCGA (PEG=1500) prepared with the use of glycolide was used in place of D,L-lactide. In the block copolymer prepared in this Example, the molecular weight ratio of PEG/PCGA was 1/2.02, and the molar fraction of CL/GA in the PCGA block was 2.38/1.

Example 9

OSM-PCGA-PEG-PCGA-OSM Block Copolymer (2)

The pentablock copolymer was prepared in the same manner as in Example 8 except that the molecular weight ratio of PEG/PCGA and the molar fraction of CL/GA in the PCGA block were changed from 1/2.02 and 2.38/1 to 1/2.23 and 2.39/1, respectively.

Test Example 1

Evaluation of Sol-gel Transition Behavior Caused by Change in pH

The block copolymers prepared according to the present invention was evaluated for their sol-gel transition behavior caused by a change in pH.

Each of the pentablock copolymers (OSM-PCLA-PEG-PCLA-OSM, OSM=1144) prepared in Examples 1 and 2 was added and dissolved in a buffer solution at 15% by weight and titrated with HCl solution to adjust the pHs of the block copolymer solutions to 8.2, 8.0, 7.8, 7.6, 7.4, and 7.2, respectively. Each of the pentablock copolymer solutions with the respective pHs was equilibrated at constant temperature for 10 minutes while increasing the solution temperature by 2° C. each time and then slanted to measure the sol-gel transition behavior. The sol-gel transition behaviors of the block copolymers, caused by changes in temperature and pH, will be described with reference to FIGS. 3 and 4.

"A", "B", "C" and "D" shown in FIGS. 3 and 4 show that the block copolymers are present under specified temperature and pH conditions. Specifically, "A" represents conditions of high temperature (37° C.), the same temperature as in vivo, and low pH (pH 7.4), "B" represents conditions of high temperature (37° C.), the same temperature as in vivo, and high pH (pH 8.0), "C" represents conditions of low temperature (15° C.) and low pH (pH 7.4), and "D" represents conditions of low temperature (15° C.) and high pH (pH 8.0).

The block copolymer present under the D conditions (15° C. and pH 8.0) showed a sol state with low viscosity due to the low hydrophobicity of the PCLA block caused by low temperature and the ionization of OSM caused by high pH (see FIGS. 3 and 4). When the temperature of the D conditions was gradually increased to the temperature of the B conditions (37° C. and pH 8.0), which is the same temperature as in vivo, the hydrophobicity of the PCLA block was then increased resulting in a slight increase in viscosity, but OSM acted as an ionized hydrophilic block so that gel was not formed (see FIGS. 3 and 4). Furthermore, when the pH of the D conditions was decreased to 7.4 with the temperature maintained at 15° C. so as to reach the C conditions (15° C. and pH 7.4), the ionization degree of OSM was then gradually reduced to increase the hydrophobicity of OSM, resulting in an increase in viscosity, but the block copolymer was maintained at the sol state without forming gel due to the low hydrophobicity of the PCLA block at low temperature (see FIGS. 3 and 4). However, in the A conditions (37° C. and pH 7.4) with the same temperature as in vivo and low pH, the block copolymers of Examples 1 and 2 all showed a gel state. This suggests that an increase in temperature results in an increase in the hydrophobicity of the PCLA block, and OSM which has not been ionized at low pH also acts as a hydrophobic block, so that the block copolymer solution according to the present invention forms gel due to a strong hydrophobic bond between the PCLA and OSM blocks.

As described above, it could be found that the inventive block copolymer showed the reversible sol-gel transition behavior not only by a change in the ionization degree of the sulfonamide-based oligomer in the copolymer with a change in pH but also by a change in the hydrophobicity of the biodegradable copolymer with a change in temperature. This indicates that the inventive block copolymer shows the reversible sol-gel transition behavior caused by changes in not only temperature but also pH.

Test Example 2

Stability Evaluation

In order to evaluate the stability of a hydrogel formed from the inventive block copolymer, the following test was performed.

The pentablock copolymer (OSM-PCLA-PEG-PCLA-OSM, OSM Mn=1144) prepared in Example 1 was adjusted to 15° C. and pH 8.0 so as to prepare a sol solution. Then, the sol solution was injected into buffer solution 1 (37° C. and pH 7.4) and buffer solution 2 (37° C. and pH 8.0) and then observed for changes in its state. Also, the pentablock copolymer solution formed gel under conditions of pH 7.4 and 37° C., and to the formed gel, an excess of a buffer solution (pH 7.4 and 37° C.) was added and the gel added the buffer solution was left to stand in a water bath (37° C.) for a long time.

In the results obtained by injecting the sol solution (15° C. and pH 8.0) formed from the block copolymer into each of the buffer solutions 1 and 2 having the same temperature as in vivo (37° C.) and different pHs, the sol solution was gelled in the buffer solution 1 (37° C. and pH 7.4) whereas it was dissolved in the buffer solution 2 (37° C. and pH 8.0) (see FIG. 5). This indicates that high temperature and low pH induce an increase in the hydrophobicities of the biodegradable polymer and the sulfonamide-based oligomer in the block copolymer, resulting in the gelling of the block copolymer.

Figure 6:
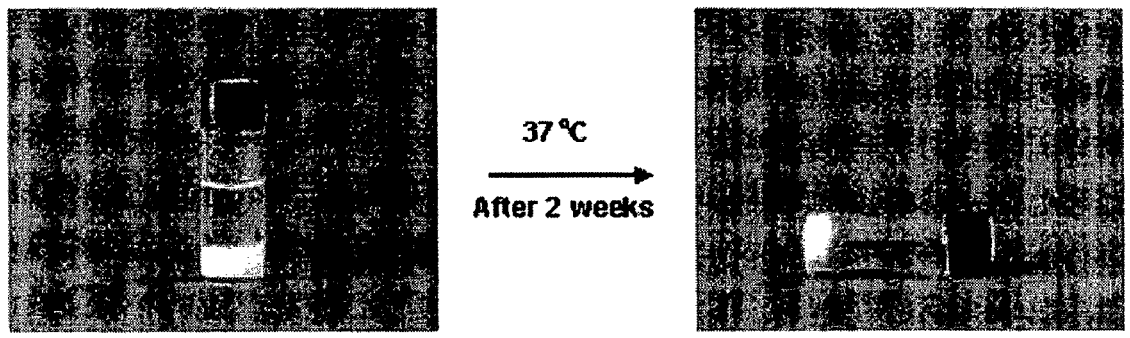
FIG. 6 depicts photographs showing the stability of a hydrogel formed from a block copolymer (OSM-PCLA-PEG-PCLA-OSM) prepared in Example 1.

Furthermore, the gel formed from the block copolymer hydrogel under conditions of high temperature and low pH (37° C. and pH 7.4) was not collapsed for at least two weeks even when an excess of the buffer solution (37° C. and pH 7.4) was added (see FIG. 6). This indicates that the formed gel is stable.

Test Example 3

Evaluation of Change in Sol-gel Phase Diagram of Block Copolymer

A change in the sol-gel phase diagram in a hydrogel formed from the block copolymer was examined by various parameters in the following manner. The parameters contain the ratio of hydrophilic to hydrophobic blocks in the block copolymer, the molecular weight of the block copolymer, and the length of the pH sensitive block, etc.

The OSM-PCLA-PEG-PCLA-OSM pentablock copolymers prepared in Examples 1, 3, 4 and 5 were used in which the molecular weights of PEGs in the block copolymers of Examples 1, 3 and 4 were 1,500, 1,750 and 2,000, respectively, and the molecular weights of OSMs in the block copolymers of Examples 1 and 5 were 1,144 and 937, respectively.

Figure 7:
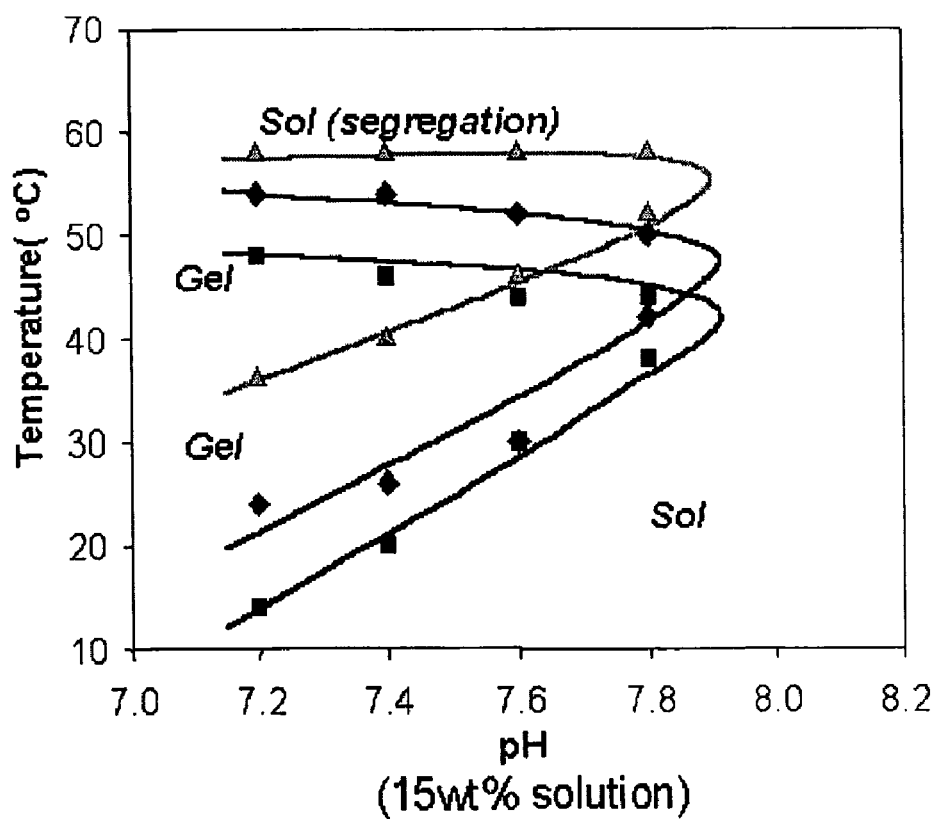
FIG. 7 is a graphic diagram showing a change in the sol-gel phase diagram of block copolymers (OSM-PCLA-PEG-PCLA-OSM) prepared in Examples 1, 3 and 4, with a change in the molecular weight of the block copolymers.

FIG. 7 depicts phase diagrams caused by increases in the molecular weights of PEG and the block copolymer in a state where the molecular weight ratio of the hydrophilic polymer PEG and the hydrophobic polymer PCLA was fixed to 1/2.1 (PEG/PCLA≅1/2.1).

It could be found that the sol-gel phase diagram of the block copolymer moves toward higher temperatures with an increase in the molecular weight of the block copolymer, but there is little or no change in a temperature range at which the block copolymer forms gel (see FIG. 7). This suggests that, when the length of the block copolymer is increased while the ratio of the hydrophilic block to the hydrophobic block is maintained at a constant ratio, the gelling of the block copolymer becomes possible by a some stronger hydrophobic condition, i.e., strong hydrophobic attraction at high temperature, in order to form a gel by the physical crosslinking caused by the attraction between the hydrophobic blocks. Also, It could be found that a temperature range at which gel is formed be affected mainly by ratio of hydrophilic to hydrophobic blocks.

Meanwhile, it was shown that, at a low pH range, a temperature range at which gel is formed was decreased with an increase in the molecular weight of the block copolymer (see FIG. 7). This is because OSM is present in a non-ionized state at low pH and thus acts as a hydrophobic block, so that the ratio of the hydrophilic block PEG to the hydrophobic block PCLA-OSM is decreased with an increase in the molecular weight of PEG. Accordingly, it could be found that, at low pH, a temperature range at which gel is formed was slightly decreased with an increase in the total molecular weight of the block copolymer.

Figure 8:
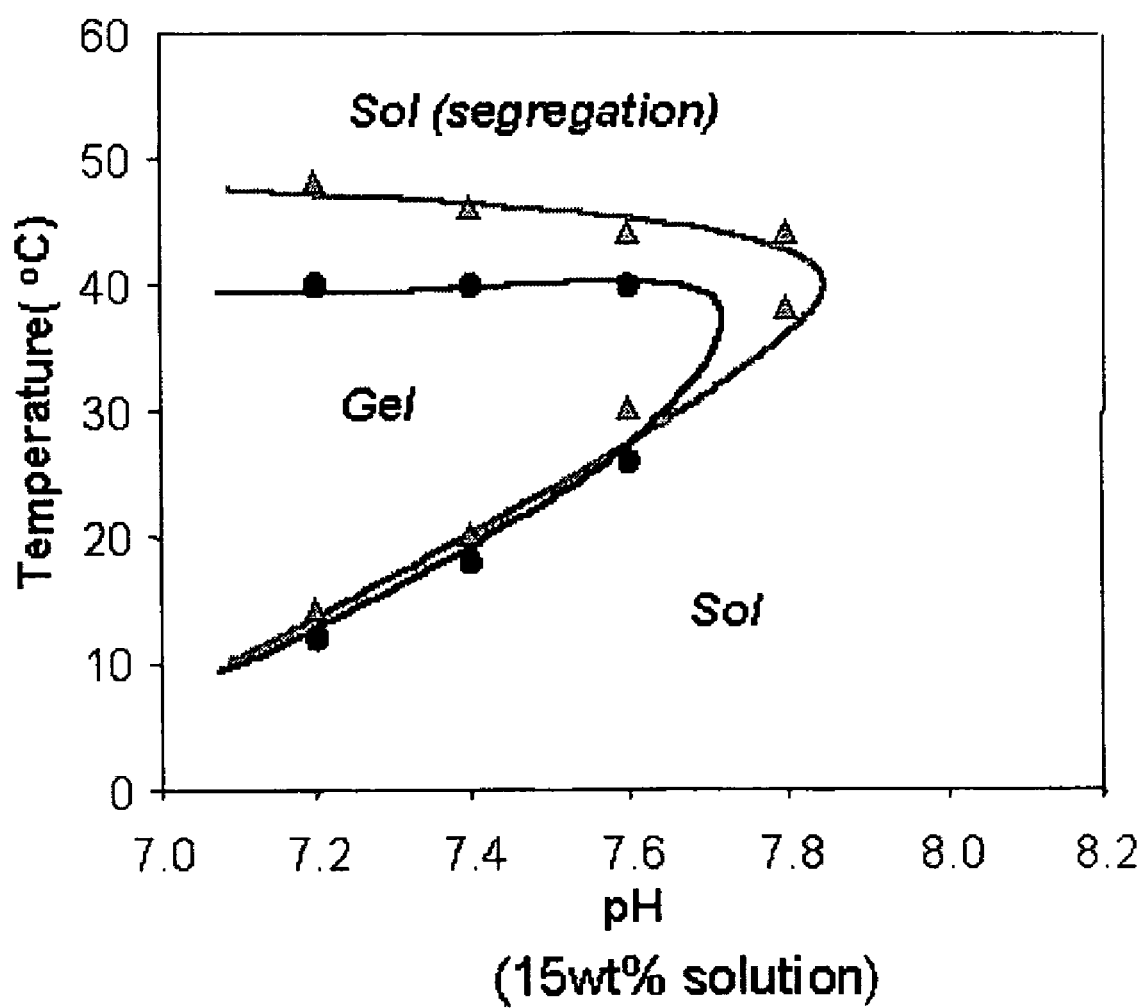
FIG. 8 is a graphic diagram showing a change in the sol-gel phase diagram of block copolymers (OSM-PCLA-PEG-PCLA-OSM) prepared in Examples 1 and 5, with a change in the molecular weight of the sulfonamide-based oligomer.

FIG. 8 depicts the sol-gel phase diagram of the OSM-PCLA-PEG-PCLA-OSM pentablock copolymer hydrogel, caused by a change in the molecular weight of OSM.

It could be found that OSM which is presented mainly in an ionized state at a high pH range was presented in a sol state regardless of its molecular weight. However, it could be seen that, with a decrease in pH, OSM was non-ionized and thus acted as a hydrophobic block, and particularly at a low pH range, the hydrophobicity of the block copolymer was increased with an increase in the molecular weight of OSM, resulting in an increase in a range at which gel is formed (see FIG. 8).

Accordingly, it could be confirmed that temperature and pH ranges at which sol-gel transition occurs can be adjusted depending on the molecular weight and composition ratio of the block copolymer.

Test Example 4

Evaluation of Sol-gel Transition of Block Copolymer Caused by Changes in Temperature and pH The sol-gel transition behavior of the block copolymer prepared according to the present invention, caused by changes in temperature and pH, was evaluated in the following manner.

The triblock copolymers (MPEG-PCLA-OSM, MPEG=750, OSM=1144) prepared in Examples 6 and 7, and the pentablock copolymers (OSM-PCGA-PEG-PCGA-OSM, PEG=1500, OSM=1144) prepared in Examples 8 and 9, were added and dissolved in buffer solutions at 25% by weight for the triblock copolymers and 15% by weight for the pentablock copolymers, and titrated with HCl solution to adjust the pHs of the solutions to 8.2, 8.0, 7.8, 7.6, 7.4, and 7.2, respectively. Each of the block copolymer solutions with the respective pHs was equilibrated at constant temperature for 10 minutes while increasing the solution temperature by 2° C. each time and then maintained at a slanted state for 1 minute. At this time, the sol-gel transition behavior of each solution was measured by determining the flowing of the solution to be sol and the non-flowing of the solution to be gel.

Figure 9:
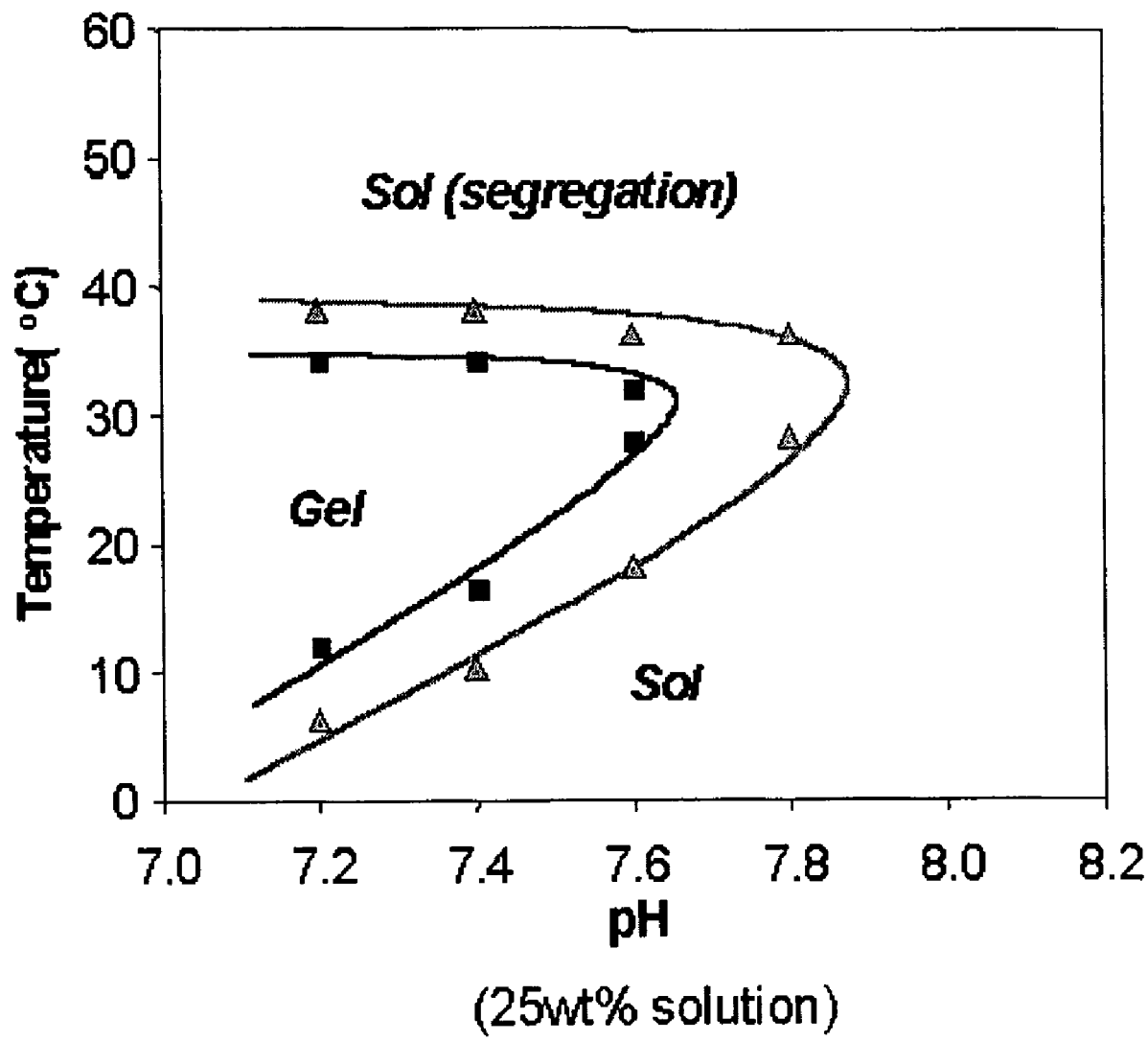
FIG. 9 is a graphic diagram showing the sol-gel transition behaviors of block copolymers (MPEG-PCLA-OSM) prepared in Examples 6 and 7, caused by changes in temperature and pH.
Figure 10:
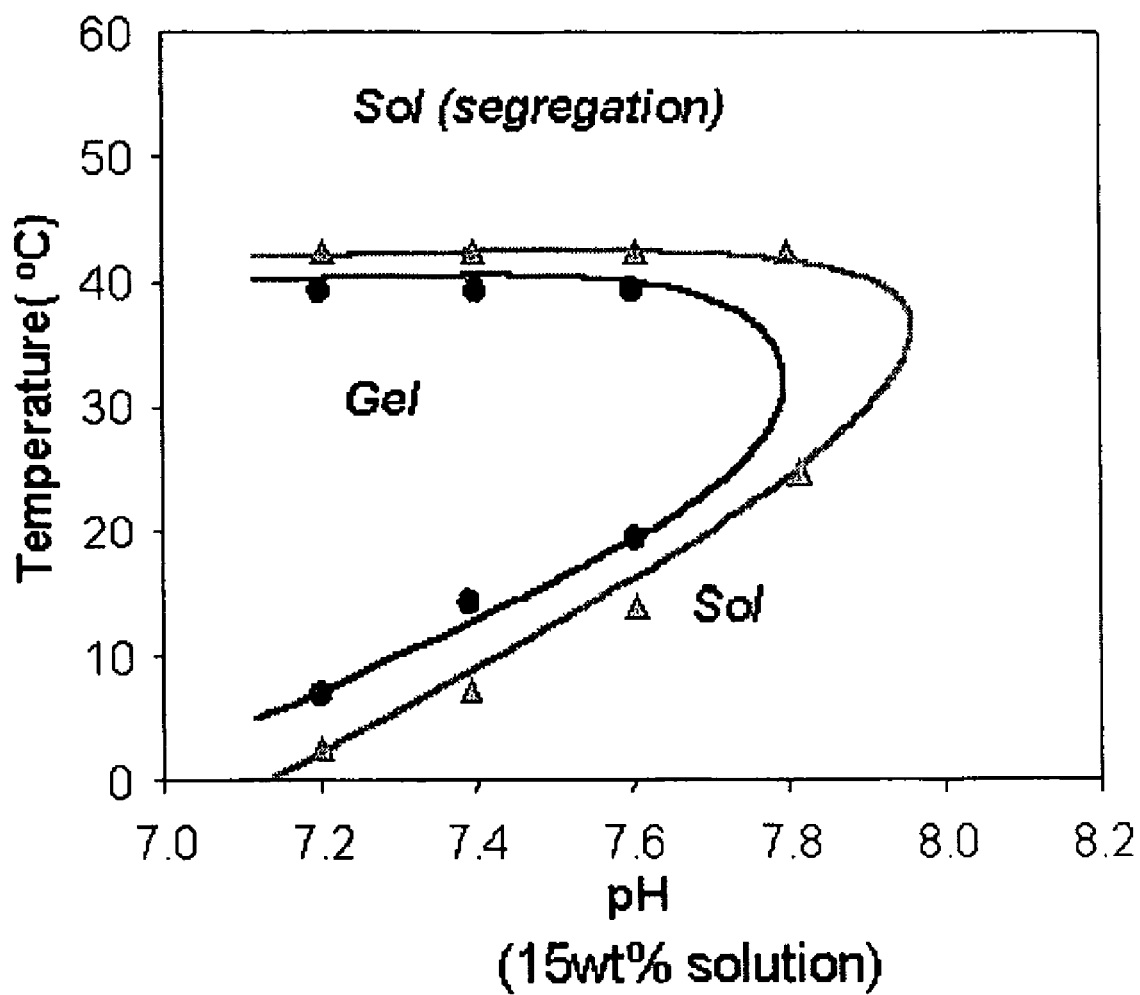
FIG. 10 is a graphic diagram showing the sol-gel transition behaviors of block copolymers (OSM-PCGA-PEG-PCGA-OSM) prepared in Examples 8 and 9, caused by changes in temperature and pH.

In the test results, the triblock and pentablock copolymers prepared in Examples 6-9 all showed the same sol-gel transition behaviors as the results of Test Example 1 (see FIGS. 9 and 10).

It can be seen that the triblock copolymers (MPEG-PCLA-OSM) prepared in Examples 6 and 7 are gelled at a higher concentration than that of the OSM-PCLA-PEG-PCLA-OSM pentablock copolymers (see FIG. 9). This is attributable to a difference in gel formation mechanism between the block copolymers. The OSM-PCLA-PEG-PCLA-OSM block copolymer having the hydrophobic blocks at both ends thereof are gelled by the interconnection between micelles formed of the block copolymer, whereas the MPEG-PCLA-OSM block copolymer is gelled by the packing of micelles formed of the block copolymer. This suggests that hydrogels are formed also at high concentration, due to the high concentration of micelles required in gel formation.

In addition, it was shown that the block copolymers (OSM-PCGA-PEG-PCGA-OSM) prepared in Examples 8 and 9 were gelled at a higher composition ratio of the hydrophobic block to the hydrophilic block than that of the block copolymer prepared in Example 1 (see FIG. 10). This is believed to be attributable to the magnitude of hydrophobicity of glycolide (GA), which is weaker than that of lactide (LA).

INDUSTRIAL APPLICABILITY

As described above, the block copolymer according to the present invention shows the sol-gel transition behavior sensitive to changes in not only temperature but also pH. Thus, the inventive block copolymer overcomes the shortcomings of temperature-sensitive copolymers, forms a more stable hydrogel at suitable temperature and pH, and also solves an in vivo stability problem with the prior block copolymers. Accordingly, the inventive block copolymer can be used in various applications in the medical and drug delivery fields.

The invention claimed is:
1. A block copolymer formed of:
(a) a copolymer of a polyethylene glycol (PEG)-based compound and a biodegradable polymer; and
(b) a sulfonamide-based oligomer,
wherein the sulfonamide-based oligomer (b) contains a hydrophilic functional group selected from the group consisting of hydroxyl and carboxyl groups at a terminal end thereof; wherein the sulfonamide-based oligomer (b) is coupled to only the biodegradable polymer in the copolymer (a) by a direct bond at the hydrophilic functional group; and
wherein the block copolymer forms hydrogel by sol-gel transition in accordance with a change in temperature and pH.

2. The block copolymer of claim 1, wherein the polyethylene glycol-based compound is represented by the following formula 1:

[Formula 1]

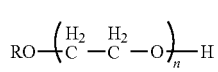

wherein R represents hydrogen or an alkyl group containing 1 to 5 carbon atoms, and n is a natural number ranging from 11 to 45.

3. The block copolymer of claim 1, wherein the molecular weight of the polyethylene glycol-based compound is 500-2,000.

4. The block copolymer of claim 1, wherein the biodegradable polymer is at least one selected from the group consisting of caprolactone, glycolide and lactide.

5. The block copolymer of claim 1, wherein the copolymer of polyethylene glycol-based compound-biodegradable polymer is at least one selected from the group consisting of polylactide, polyglycolide, polycaprolactone, poly(caprolactone-lactide) random copolymer (PCLA), poly(caprolactone-glycolide) random copolymer (PCGA), and poly(lactide-glycolide) random copolymer (PLGA).

6. The block copolymer of claim 1, wherein the molecular weight ratio of the PEG-based compound to the biodegradable polymer is 1:1-3.

7. The block copolymer of claim 1, wherein the sulfonamide-based oligomer is formed from a sulfonamide-based compound which is at least one selected from group consisting of sulfamethisole, sulfamethazine, sulfasetamide, sulfisomidine, sulfaphenazole, sulfamethoxazole, sulfadiazine, sulfamethoxydiazine, sulfamethoxypyridazine, sulfadoxine, sulfapyridine, sulfabenzamide and sulfisoxazole.

8. The block copolymer of claim 1, wherein the molecular weight of the sulfonamide-based oligomer is 500-2,000.

9. The block copolymer of claim 1, which is a triblock or higher order multiblock copolymer.

10. The block copolymer of claim 9, which is a triblock or pentablock copolymer.

11. The block copolymer of claim 1, which is represented by the following formula 2:

[Formula 2]

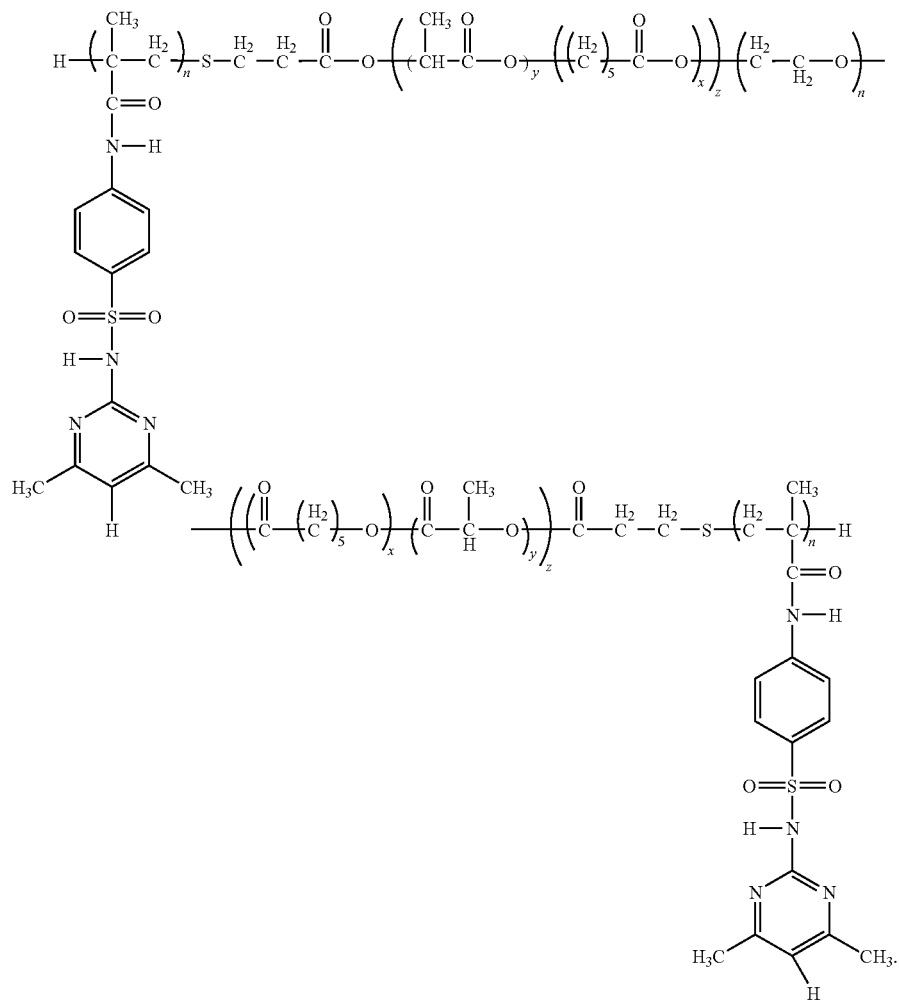

12. The block copolymer of claim 1, which is represented by the following formula 3:
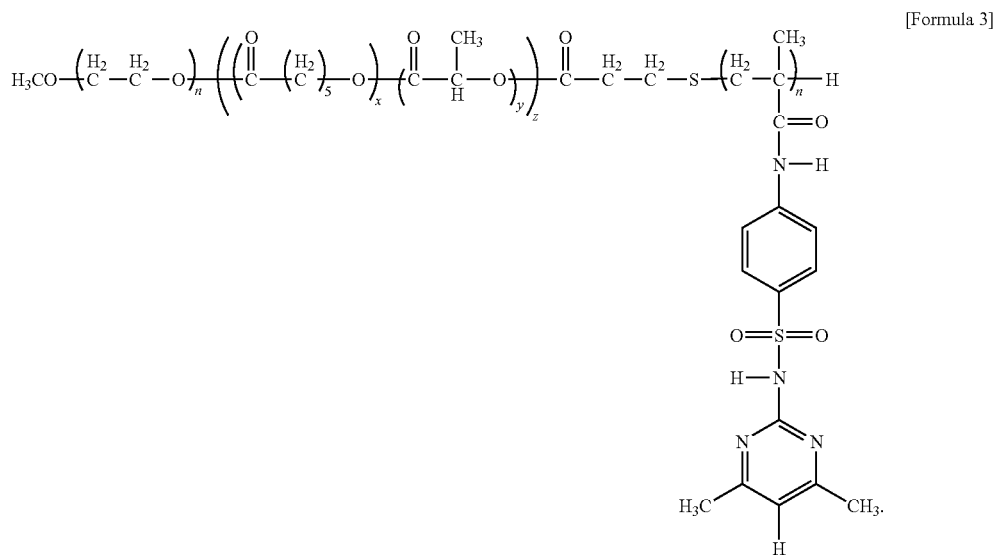
[Formula 3]
13. The block copolymer of claim 1, which is represented by the following formula 4:
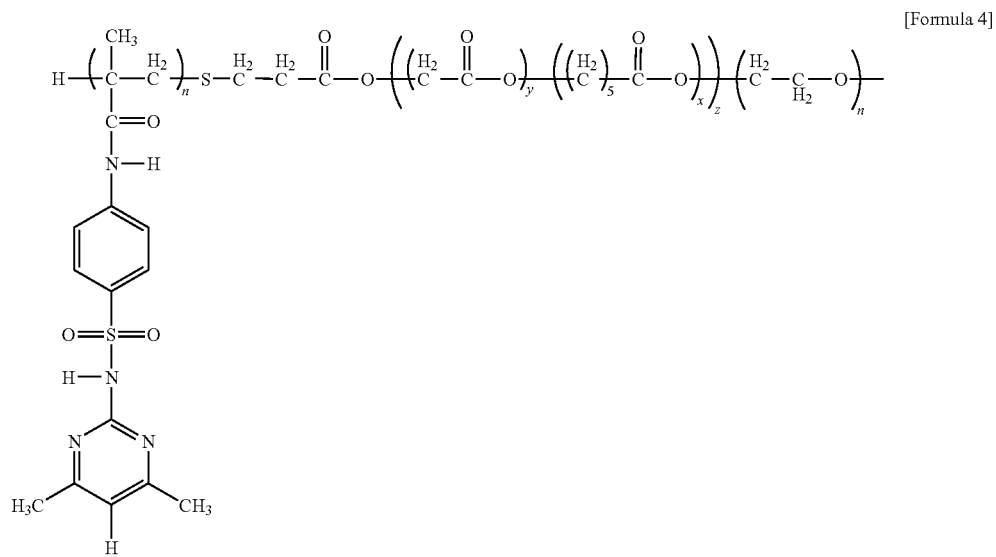
[Formula 4]

-continued
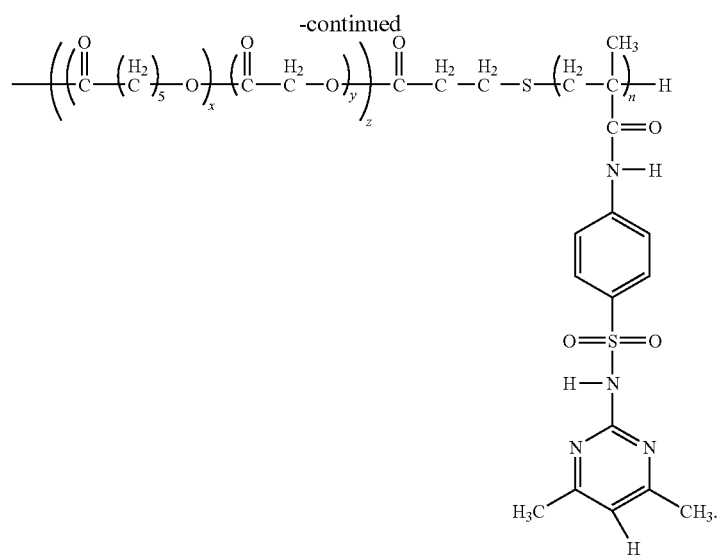
14. A hydrogel composition comprising a block copolymer as claimed in any one of claims 1-6 and 7.
15. A hydrogel formed from a hydrogel composition as claimed in claim claim 14.
* * * * *